(12) United States Patent
Bousack et al.

(10) Patent No.: US 6,300,759 B1
(45) Date of Patent: Oct. 9, 2001

(54) DEVICE AND METHOD FOR SUPPRESSING SIGNALS WHEN INSPECTING PRESTRESSED CONSTRUCTION ELEMENTS

(75) Inventors: Herbert Bousack; Hans-Joachim Krause, both of Aachen; Gottfried Sawade, Stuttgart, all of (DE)

(73) Assignees: Forschungszentrum Jülich GmbH, Jülich; Forschungs- und Materialprüfungsanstalt Baden-Württemberg, Stuttgart, both of (DE)

( * ) Notice: Subject to any disclaimer, the term of this patent is extended or adjusted under 35 U.S.C. 154(b) by 0 days.

(21) Appl. No.: 09/230,694
(22) PCT Filed: Jul. 31, 1997
(86) PCT No.: PCT/DE97/01620
§ 371 Date: Jan. 29, 1999
§ 102(e) Date: Jan. 29, 1999
(87) PCT Pub. No.: WO98/05952
PCT Pub. Date: Feb. 12, 1998

(30) Foreign Application Priority Data

Aug. 3, 1996 (DE) .............................. 196 31 490

(51) Int. Cl.⁷ .................................................. G01N 27/72
(52) U.S. Cl. .......................... 324/225; 324/238; 324/240
(58) Field of Search ..................................... 324/238, 235, 324/251, 239, 240, 262, 228, 241, 242, 243, 225

(56) References Cited

U.S. PATENT DOCUMENTS

| 4,503,393 | 3/1985 | Moyer et al. . | |
|---|---|---|---|
| 4,573,013 | * 2/1986 | Kusenberger et al. | 324/238 |
| 4,739,273 | * 4/1988 | Petersen et al. | 324/242 |
| 4,837,509 | * 6/1989 | Dodmann et al. | 324/207 |
| 5,545,987 | * 8/1996 | Schutt et al. | 324/219 |
| 5,720,140 | * 2/1998 | Bousack et al. | 52/223.14 |

FOREIGN PATENT DOCUMENTS 40 37 992   6/1992   (DE) .

* cited by examiner

Primary Examiner—Christine K. Oda
Assistant Examiner—Subhash Zaveri
(74) Attorney, Agent, or Firm—Collard & Roe, P.C.

(57) ABSTRACT

A test device and process for inspecting the integrity of prestressed construction elements. The device comprises a testing head having a magnetization device for generating a magnetic field around the construction element. The testing head is connected to a controller device for controlling the magnetization process and for processing signals corresponding to the magnetic field. The testing head magnetizes the construction element over a predetermined measurement section. The controller switches the magnetization device after the magnetization process is completed and then stores and processes the signals recorded.

5 Claims, 10 Drawing Sheets

DEVICE AND METHOD FOR SUPPRESSING SIGNALS WHEN INSPECTING PRESTRESSED CONSTRUCTION ELEMENTS

BACKGROUND OF THE INVENTION

1. Field of the Invention

The present invention relates to a test arrangement for inspecting the integrity of concrete parts such as, for example the prestressing steel of prestressed concrete construction elements, with a testing head, which has a magnetization device for generating a magnetic field around the construction element, and with a controller for controlling the magnetization process and for processing the signals corresponding with the magnetic field; as well as to a device for such an inspection.

2. The Prior Art

Fractures of the prestressing reinforcement are detected through characteristic anomalies of the magnetic field surrounding the construction element. Such anomalies are based on local variations of the magnetization, or of the magnetic permeability of the prestressing reinforcement. The magnetic field is measured in the course of the magnetization process (measurement in the active field), or after the magnetization process (measurement of the residual field). The problem with the evaluation of the magnetic stray field signals lies in the fact that fracture signals, if any, are superimposed by the signals of the slack reinforcement near the surface.

The test arrangement and the method of magnetic stray field measurement have been employed for some time now for non-invasive inspection of the integrity of the prestressing reinforcement of concrete construction elements. The stray field signals are primarily influenced by the cross girders. Since the construction element is tested from the surface bia a testing head, the spacing of the cross girders from the testing head is smaller than the spacing of the prestressing reinforcement from the testing head. The amplitudes of the girders signals are consequently higher than the emplitudes of the fracture signals—if any—in most cases.

When measuring in the active field, fractures of the pre-stressing reinforcement can be detected by the method of measuring at different magnetization field intensities. Use is made in this connection of the saturation behavior of ferromagnetic materials; the reinforcement near the surface reaches magnetic saturation earlier than the reinforcement located in deeper zones.

Fracture detection thus takes place by this method through the comparison of signals (correlation analysis; weighted signal difference) of measurements that were carried out at different magnetization field intensities. However, the measuring signal still always contains here the signals of the cross girders.

For suppressing the girder signals in residual field measurements, the cross girders are demagnetized with test arrangements and methods of the state of the art by controlling the magnetization process in numerous steps in a manner not described in detail, so that only the signals of a longitudinal reinforcement or prestressing reinforcement will be left. However, it is possible here too that the longitudinal reinforcement is at least partly demagnetized as well, and that possible fracture signals are therefore not detected.

SUMMARY OF THE INVENTION

Therefore, the problem of the present invention is to provide a test arrangement and a method by which the signals of the cross girders can be eliminated by way of calculation without having to carry out any active demagnetization of the construction element.

The problem is solved in that the testing head magnetizes the construction element over a predetermined measurement section in two successive magnetization operations with opposite polarities, and that the controller switches off the magnetization device after a magnetization process with one polarity is completed, and stores and processes the signals recorded over the measurement section after the magnetization device has been switched off.

The advantage offered by the test arrangement and the method as defined by the invention as compared to active demagnetization of the cross girders (for example through application of counter fields, or alternating magnetic fields) according to the state of the art is that the pole intensity "P" of the magnetization device may remain constant in the magnetization process. This omits costly controlling of the pole intensity of the magnetization device during demagnetization of the girders, which, under certain circumstances, may influence also the magnetization of the longitudinal reinforcement and particularly of the prestressing reinforcement. On the other hand, only two magnetization operations are required as compared to the state of the art described above. This means that the inspection expenditure can be substantially reduced.

A further advantage consists in that the testing head can move with the magnetization device along the construction element to be inspected, whereby the magnetic field of said magnetization device can be described in first approximation by the field of a yoke magnet.

A further advantage consists in that the testing head is arranged in such a way that it is displaceable in directions opposing each other at least partially in order to generate in this way in the construction element magnetizations with different polarities.

A further advantage consists in that the controller superimposes the signals of the magnetization with different polarities by way of calculation, which cancels the signals of the cross girders.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limit of the invention.

FIG. 1a is a schematic front view of a typical prestressed concrete girder.

FIG. 1b is a schematic side view of the prestressed concrete girder shown in FIG. 1a.

DETAILED DESCRIPTION OF THE PREFERRED EMBODIMENT

Figures 1A, 1B:
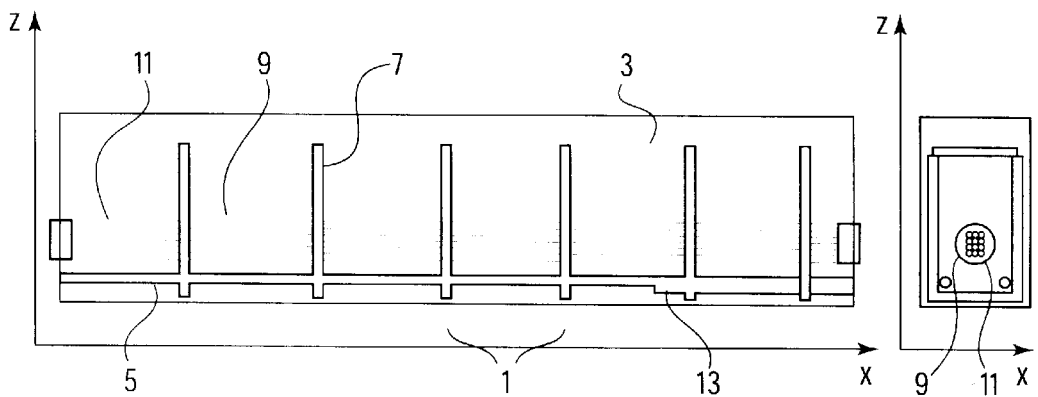

FIG. 1a shows a front view of the typical structure of a prestressed concrete girder. A reinforcement is embedded in concrete 3. In detail, said reinforcement is composed of a longitudinal reinforcement 5, cross girders 7, an envelope tube 9 with prestressing reinforcement 11, and an overlap joint 13. FIG. 1b shows the prestressed concrete girder from FIG. 1a by a side view in order to show the arrangement in terms of space, which is known per se. The structure of such a prestressed concrete girder is generally known and therefore not described herein in greater detail.

Figure 2:
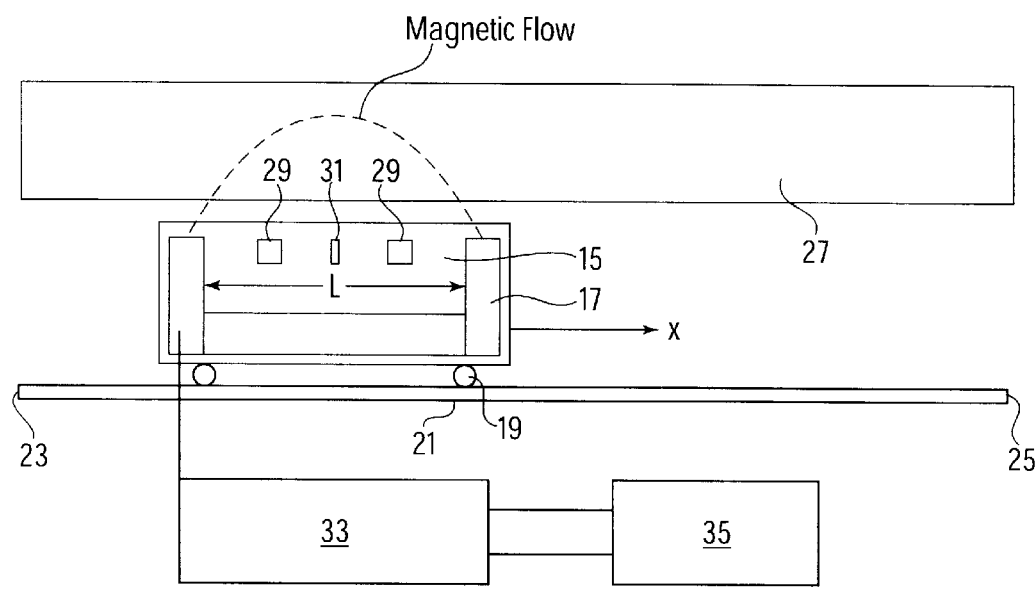
FIG. 2 is a schematic view of a test arrangement with a testing head for measuring the magnetic stray field according to the present invention.

FIG. 2 shows a schematic view of the test arrangement as defined by the invention. A testing head 15 comprises a magnetization device 17 which, in the present case, is an electromagnet with a yoke length "L". Testing head 15 is supported on the rollers 19 on a measurement section 21 designed in the form of a rail. Length "x" of measurement section 21 is predetermined. In FIG. 2, a starting point 23 is located at the left end of measurement section 21, and an end point 25 at the right end. Testing head 15 is arranged and aligned below a construction element 27 to be tested. The path of movement of testing head 15 preferably extends parallel with the surface of the underside of construction element 27.

Two pickup coils 29 and a magnetic field sensor 31 are arranged in the upper region of testing head 15.

Testing head 15 is actively connected to a controller 33. In the present embodiment, controller 33 is externally connected to testing head 15 via a line 35. However, it is conceivable also to integrate controller 33 in testing . head 15. Controller 33 is designed in such a way that it both drives the testing head 15 and switches the magnetization device 17 on and off. Furthermore, controller 33 is connected to a signal processing unit 35. The signal curves of individual magnetic fields and, in the present case, particularly the residual fields are stored in a memory area 37 of signal processing unit 35, and called off as required for further processing.

The magnetic flow through the construction element is indicated in FIG. 2 by a dashed line. The magnetic field of magnetization device 17 is described in a location determined by the coordinates x (length), y (width) and z (height) by the following relations:

$$\underline{H_0} = -P \cdot grad \left[ \frac{1}{r_1} - \frac{1}{r_2} \right] \quad (1)$$

$$r_{1,2} = \sqrt{(x_h mL/2 - x)^2 y^2 + z^2}$$

P is the pole intensity, L is the length of the yoke, and $x_h$ is in this connection the position of the center of the yoke magnet or magnetization device 17. Furthermore, it is assumed in equation (1) that the poles of the yoke magnet have the coordinates $Z_h = Y_h = 0$.

Figure 3:
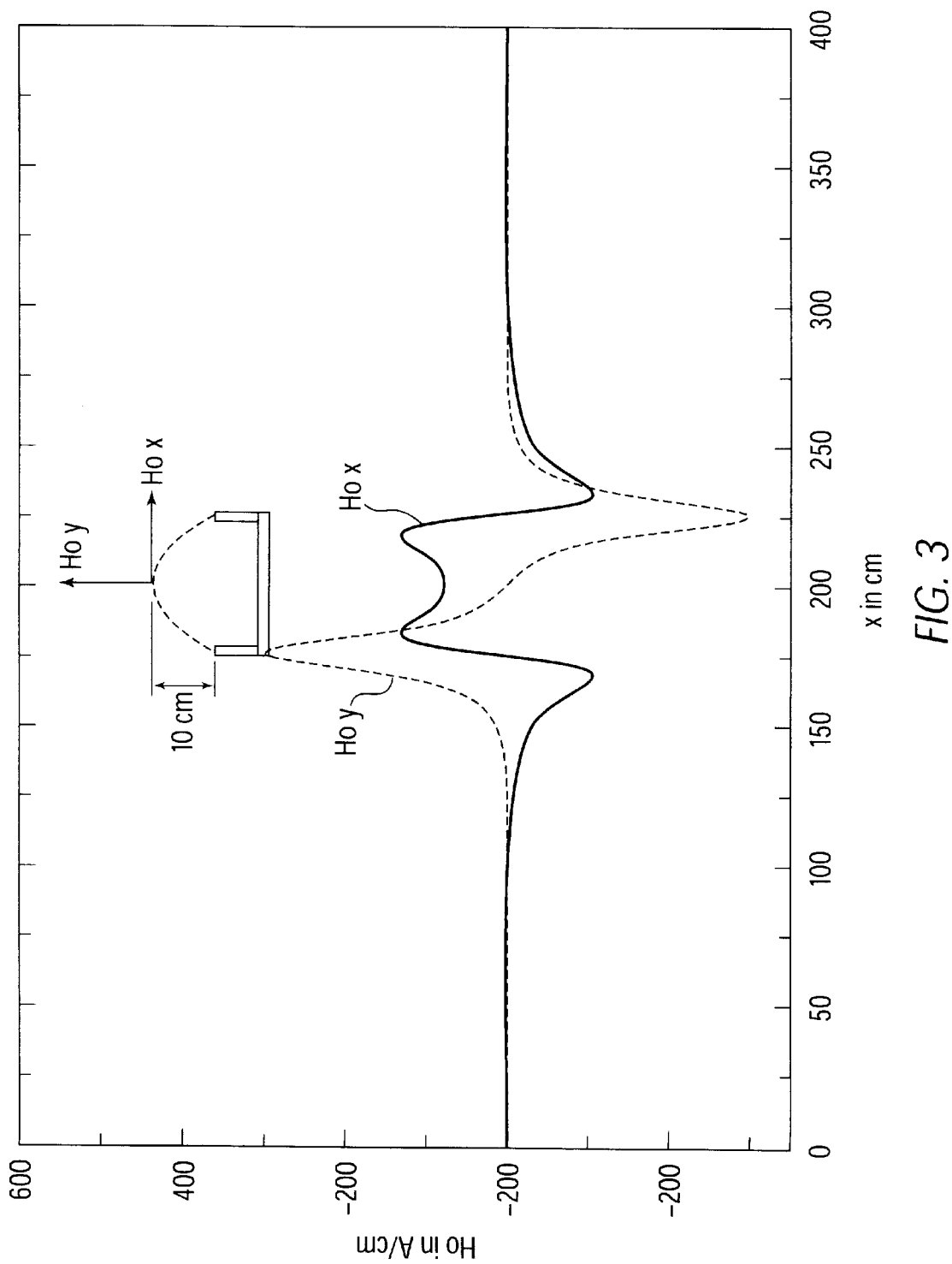
FIG. 3 is a diagram of the magnetic field Ho of the testing head with the spacing y=10 cm from the center of the testing head.
Figure 4:
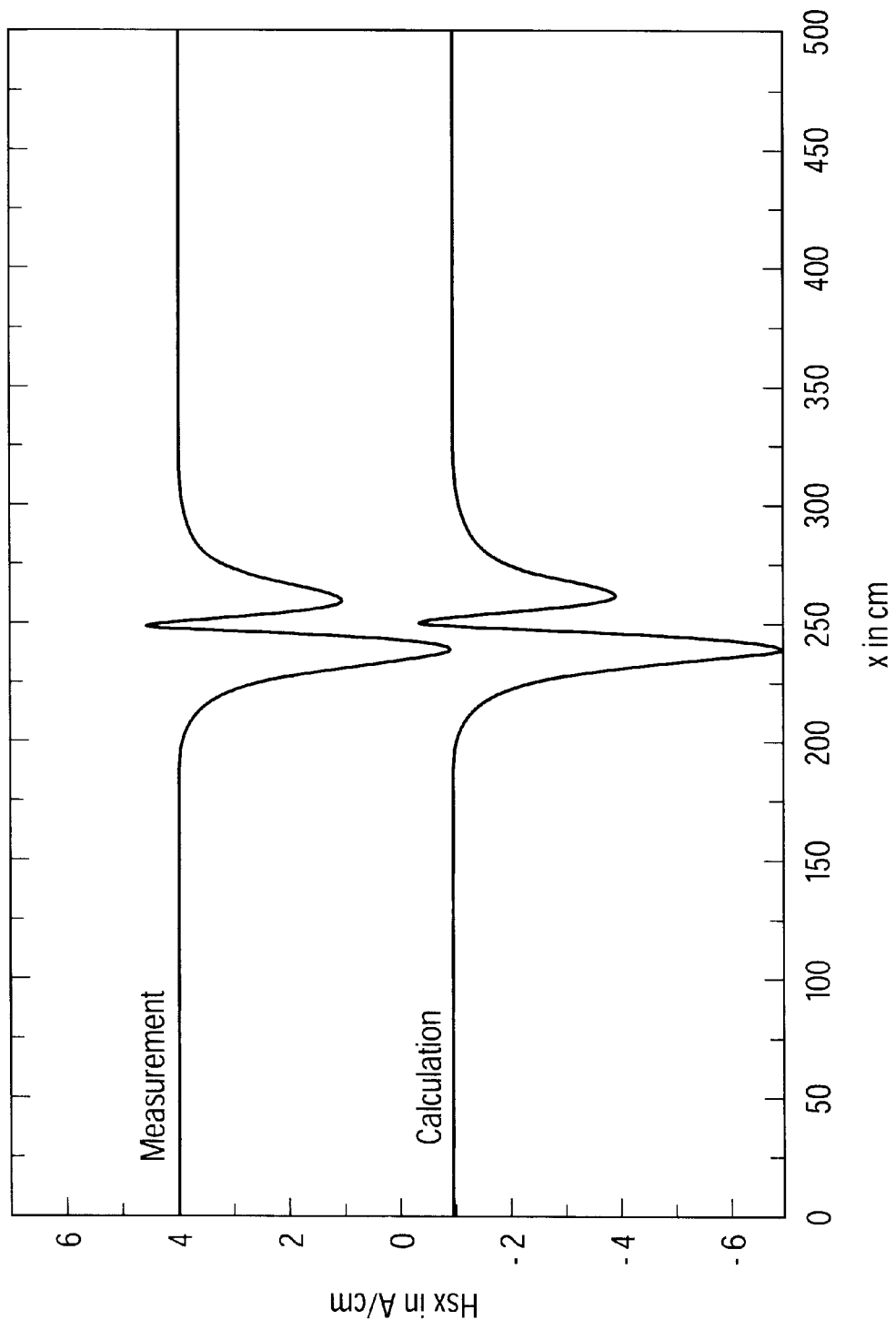
FIG. 4 is a diagram of the curve of the stray field of a cross girder measured during the forward drive in the active field.
Figure 5:
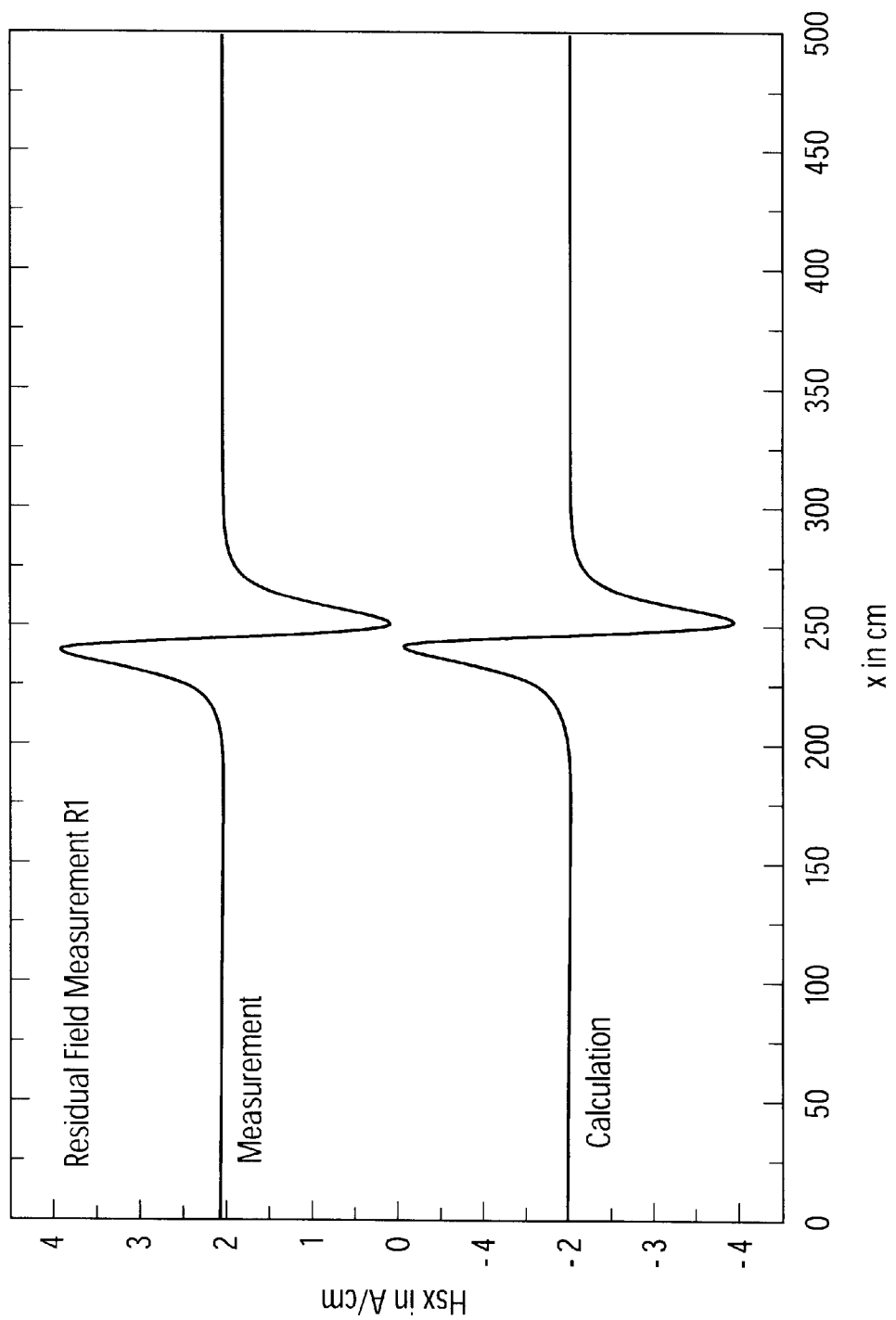
FIG. 5 is a diagram of the curve of the stray field of a cross girder of a first residual field measurement R1 after the magnetization device has been switched off at an end point of a predetermined measurement section.
Figure 6:
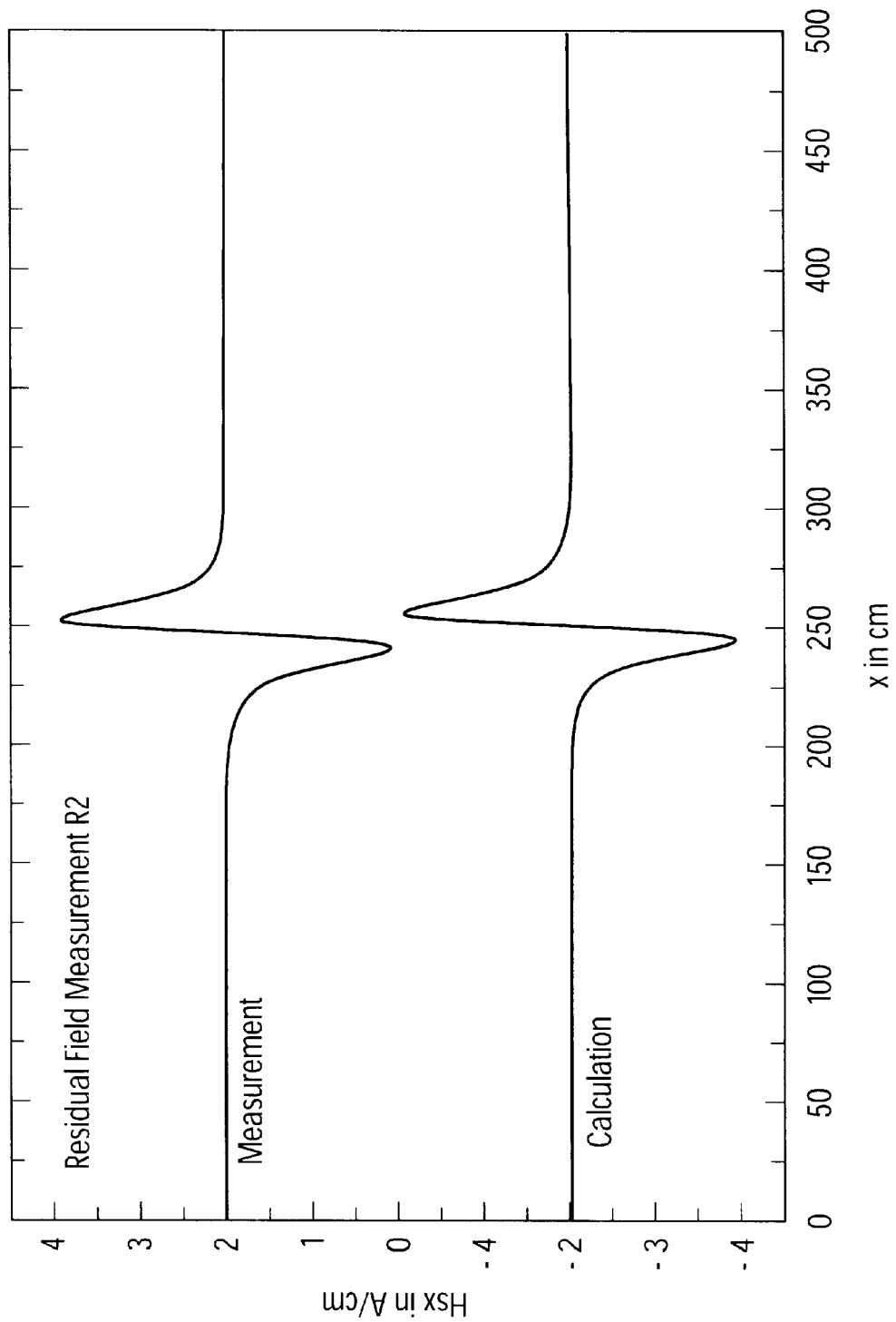
FIG. 6 is a diagram of the curve of the stray field of a cross girder of a second residual field measurement R2 after the magnetization device has been switched off at the starting point of the measurement section from FIG. 5.
Figure 7:
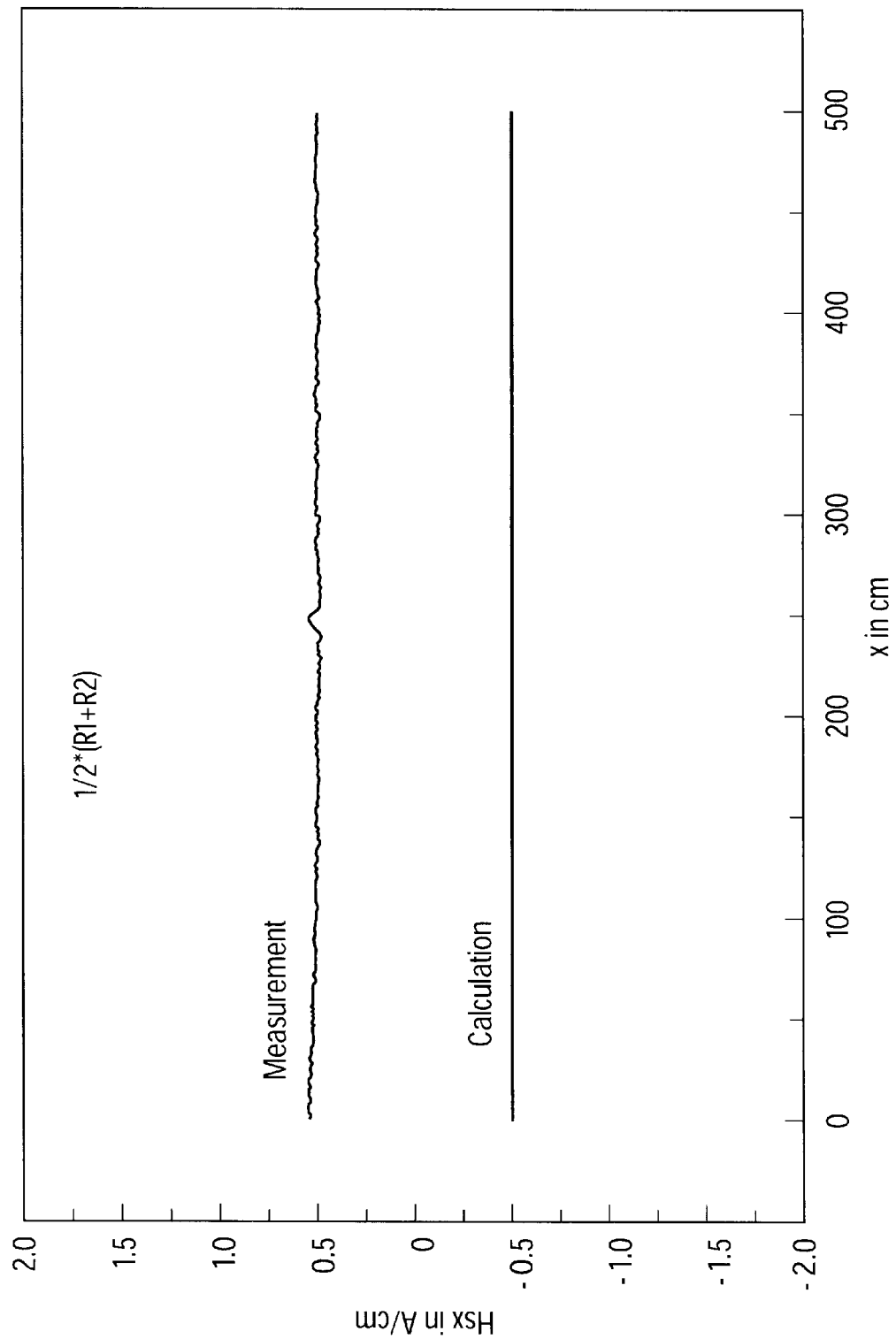
FIG. 7 is the diagram of an averaged signal curve of the residual field measurements R1 and R2 from FIG. 5 and FIG. 6.

FIG. 3 shows the vertical y- and the axial x-component of the magnetic field, whereby the center of the yoke is arranged at x=200 cm, and the vertical spacing from the plane of the pole amounts to 10 cm.

Due to the geometric demagnetization factor of the transverse and longitudinal reinforcements 7, 5, which have to be viewed as long-stretched ellipsoids, it can be assumed that the prestressing reinforcement 11 arranged lengthwise relative to the x-axis is magnetized by the axial field component Hox, whereas the cross girders 7, however, are magnetized by the vertical field component Hoy. FIG. 3 shows that the vertical field component Hoy is anti-symmetric with respect to the center of the yoke. When the testing head 15 drives past a cross girder 7, the magnetism of the latter is reversed provided the intensity of the magnetization field suffices. The sign of the residual field signal of cross girder 7 therefore is dependent upon whether in the preceding magnetization operation, the magnetic field of testing head 15 was switched on only during the forward drive and is switched off at end point 25 of measurement section 21 (case R1), or whether the magnetic field is switched on during the forward drive and the return drive and the magnetization device 17 is switched off at starting point 23 of the measurement (case R2 ).

Stray field curves (x-component) calculated and measured in this connection are plotted in FIGS. 4 to 7. Said curves are measured by a sensor 31 arranged in the center in testing head 15 as it drives past a cross girder 7. The calculations were carried out with a nonlinear program for simulating stray field measurements. The following limiting conditions were selected for the measurements:

Measurement section 21: Start of measurement at xo=0 cm
   End of measurement at xl=500 cm
Magnetization device 17 Pole intensity: P=75000 Acm
   Yoke length L=50 cm
Cross girder 7 (x=250 cm): Diameter=1 cm
   Length=50 cm
   Spacing from testing head 15:7.0 cm It is obvious that the signal of cross girder 7, when measured in the active field, differs significantly from the form of the signal in the residual field measurement; however, the amplitudes are in the same order of magnitude. Identical signals forms are obtained in the residual field measurements R1 and R2, but with different signs. The signals of cross girders 7 almost cancel each other when an average value is formed based on both measurements. This can be seen especially in FIG. 7.

Figure 8:
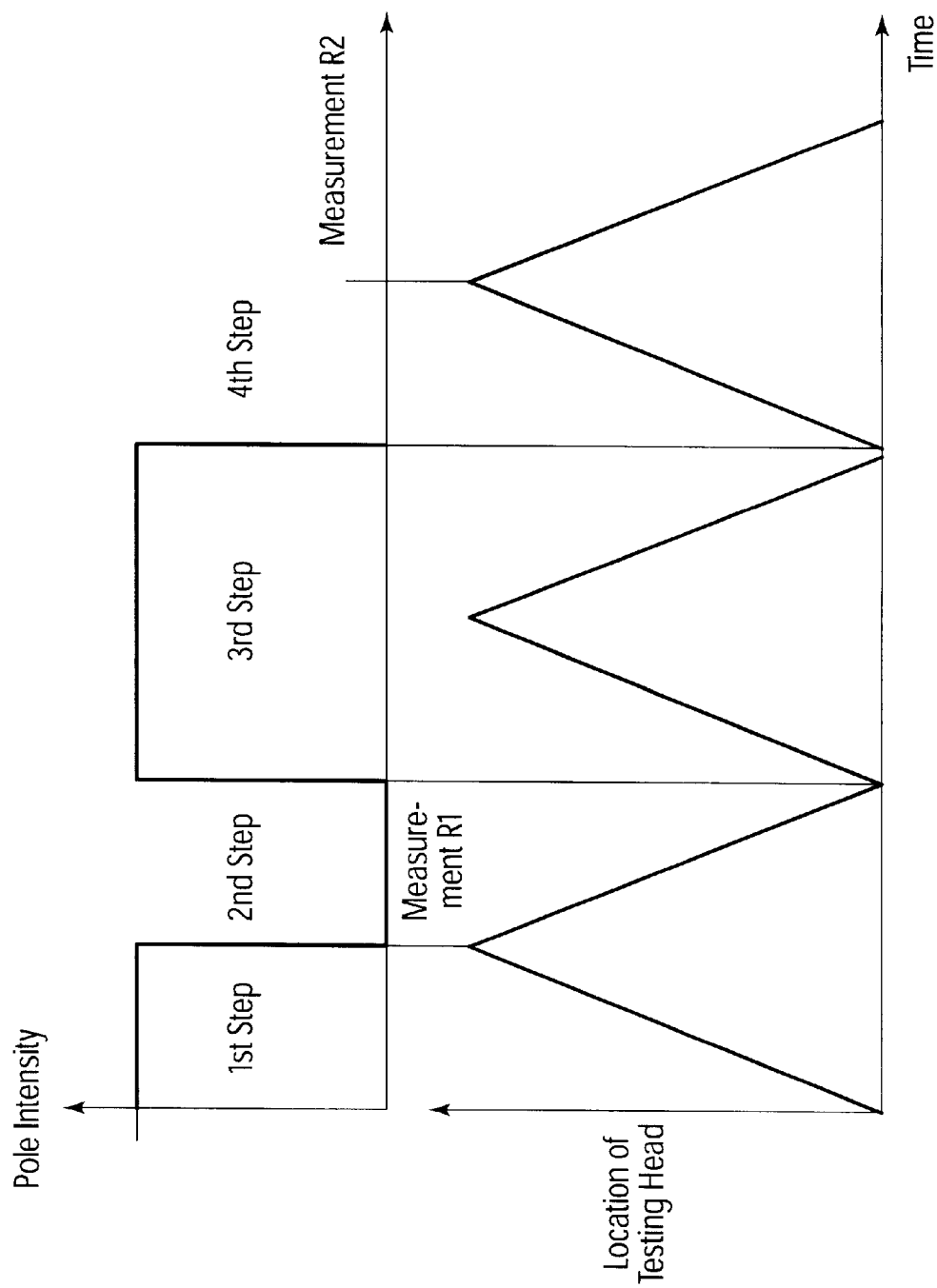
FIG. 8 is a schematic diagram of the sequence of the process as defined by the present invention.

The important steps of the process sequence for eliminating the signals of the cross reinforcement according to FIG. 8 are described in detail in the following.

1st Step: Magnetization
   Testing head 15 is driven with a constant magnetic field (poe intensity P=Po) switched on, from starting point 23 to end point 25 of measurement section 21, and switched off there (at the end point)(pole intensity P=0).

2nd Step: Residual field measurement R1(x)
   The residual field measurement is carried out at pole intensity P=0 as testing head 15 is returning, or as testing head 15 is driving again forward up to end point 25. Storage of the measured values in dependency of location x.
3rd Step: Renewed magnetization
Testing head 15 is driven with the magnetic field switched on (pole intensity P=Po) from starting point 23 to end point 25 and back again to starting point 23 and switched off there (at starting point 23).
4th Step: Residual field measurement R2(x)
A residual field measurement is carried out again at pole intensity P=0 during the return drive or while testing head is driving again forward. Storage of the measured values in dependency of location x.
5th Step: Mathematical averaging R(x)
Mathematical superposition by addition of the two measurements R1 and R2 on each location coordinate x of measurement section 21:

$$R(x) = \tfrac{1}{2}(R1(x) + R2(x)). \qquad (2)$$

Almost only the signals of the reinforcements arranged along the direction of displacement are thus still present in dataset R(x).

Figure 9:
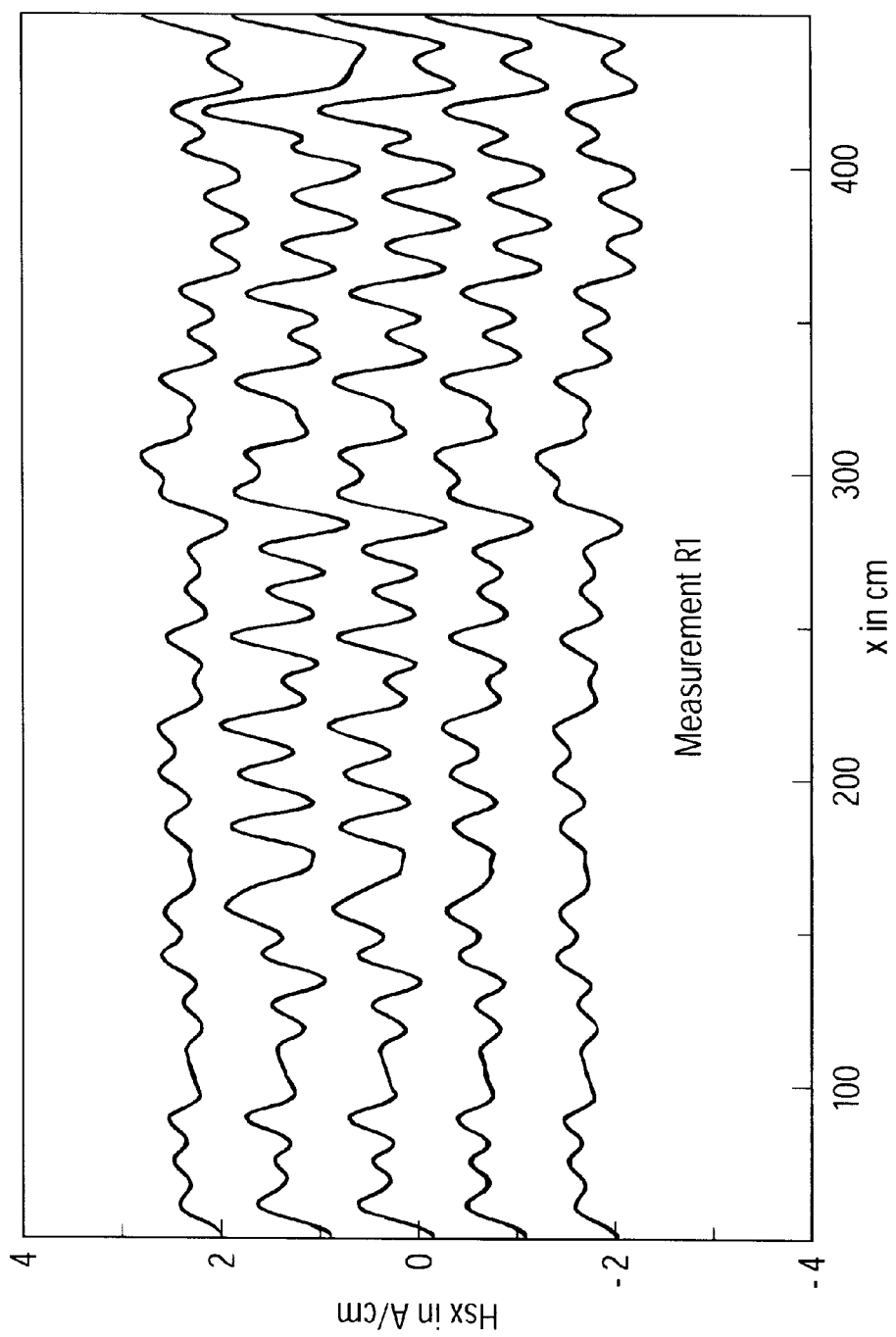
FIG. 9 is a diagram of a first residual field measurement R1 of an example with application of the test arrangement and process as defined by the present invention.
Figure 10:
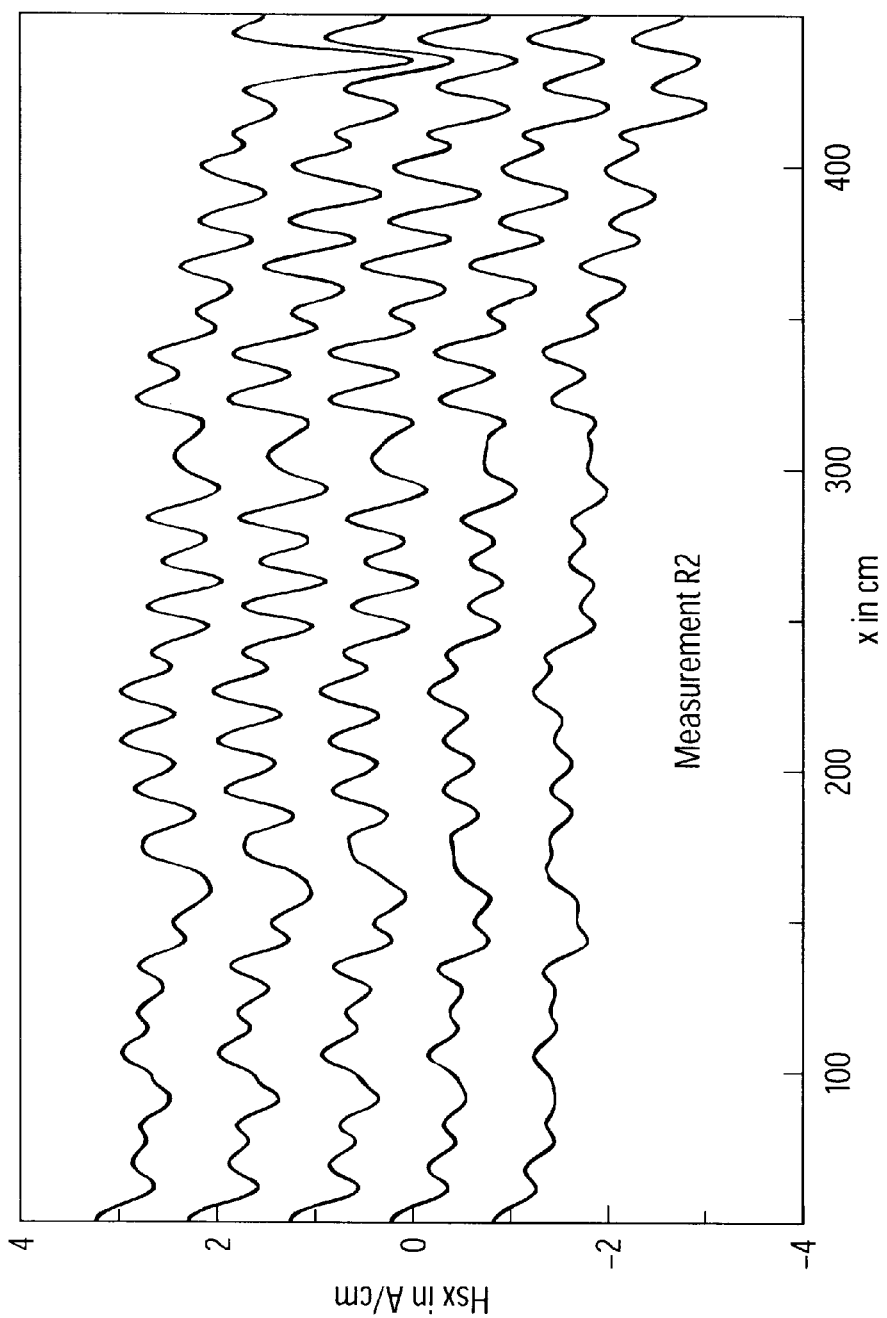
FIG. 10 is a diagram of a second residual field measurement R2 of the example from FIG. 9.
Figure 11:
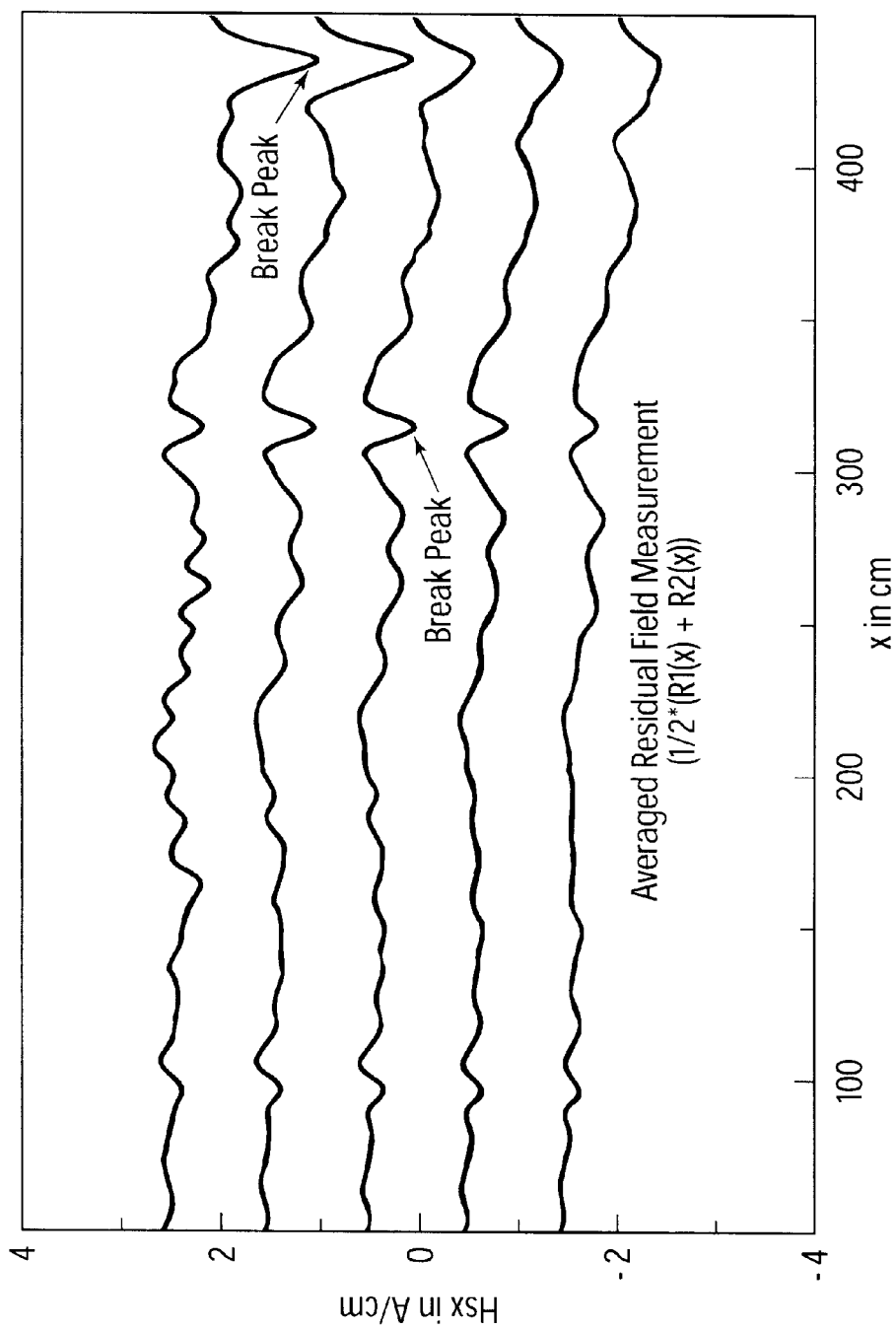
FIG. 11 is a diagram of an averaged signal curve of the residual field measurements R1 and R2 from FIG. 9 and FIG. 10.

The process is now demonstrated in the following on a practical example, in which a prestressed concrete girder 1 was inspected. The magnetic field measurement was carried out in this connection with five sensors 31, which were arranged next to each other with a spacing of 4 cm in between. The residual field measurements R1 and R2 are represented in FIGS. 9 and 10.

The averaged residual field measurement reveals two fracture locations at x=310 and x=440 cm. The fracture at x=310 is located in the center and the fracture at 440 cm is located on the edge of girder 1. The example clearly shows that it is possible by the method represented here to detect in the residual field measurement fracture signals of longitudinal reinforcement 5 which are not visible in the direct residual field measurement (R1 or R2 ).

The important features of the invention are summarized as follows:

1. Controlling of the measuring sequence according to the flow chart according to FIG. 8, whereby two residual field measurements are carried out in which the magnetizations of all reinforcements (cross girders) arranged transversely to the longitudinal reinforcement have opposite polarities.

2. Determination of the new measuring signal by forming the average value according to equation (2), in which the signals of the cross girders are largely eliminated and which substantially still contains only the residual field signal of the reinforcements arranged lengthwise.

3. Elimination of the residual field signals of the reinforcements arranged lengthwise by application of the measuring process in measuring directions extending vertically relative to the first measuring direction.

According, while only one embodiment of the present invention has been shown and describe, it is obvious that many changes and modifications may be made thereunto without departing from the spirit and scope of the invention.

What is claimed is:

1. A test device for suppressing signals when inspecting a prestressed construction element having a prestressing reinforcement and a transverse stirrup, comprising:
   a testing head (15) for magnetizing the construction element (27) over a predetermined measurement section (21) in two successive magnetization operations by switching a testing head (15) in opposite direction of each other for opposite polarities with opposite polarities;
   a magnetization device (17) disposed on said testing head for generating a magnetic field around the construction element, said magnetizing device being movable between a starting point (23) and an end point (25) of a range of measurement, said magnetic field comprising an axial field component (H0x) which magnetizes the prestressing reinforcement and a vertical field component (H0y) which magnetizes the transverse stirrups (7);
   a controller (33) attached to said testing head for controlling the magnetization, wherein said controller switches off the magnetization device (17) at said starting point (23) and at the end point (25); and
   a signal processing device (35) connected to said controller (33) for performing a residual field measurement and storing available residual field signals (R1, R2) of said vertical field component after said magnetizing device is switched off, wherein said controller mathematically superimposes said residual field signals (R1, R2) stored after the magnetizing process.

2. The test device according to claim 1, wherein said control device (33) generates an output test signal by forming a mean value following said mathematical superimposition of the individual residual field signals (R1, R2).

3. The test device according to claim 1, wherein said magnetization device (17) magnetizes the transverse stirrups (7) in said magnetizing processes across driving sections opposing one another.

4. The test device according to claim 1, wherein said magnetization device (17) is drivably disposed between said starting point (23) and said end point (25) of said measuring range (21) in directions opposing one another.

5. A method for suppressing signals when inspecting a prestressed construction component having a transverse stirrup and a prestressing reinforcement, comprising the steps of:
   generating a magnetic field (H0) between a starting point and an end point of a measuring range with a magnetization device, said magnetic field comprising an axial field component (H0x) which magnetizes the prestressing reinforcement, and a vertical field component (H0y) which magnetizes the transverse stirrups;
   switching on said magnetizing device at said starting point of said measuring range for a first magnetizing drive in a first driving direction over said measuring range;
   switching off said magnetizing device at said end point of said measuring range;
   measuring a first residual field signal (R1) of said vertical field component (H0y) of said first magnetizing drive;
   storing said measured first residual field signals (R1) of the transverse stirrups;
   switching on said magnetizing device at said starting point of said measuring range for a second magnetizing drive in an opposite driving direction over said measuring range;
   switching off said magnetizing device at when it returns to said starting point of said measuring range;
   measuring a second residual field signal (R2) of said vertical field component (H0y) of said second magnetizing drive;
   storing said measured second residual field signals (R2) of the transverse stirrups; and
   processing said stored first and second residual field signals (R1) and (R2) after the magnetizing device is switched off wherein a controller mathematically superimposes the residual field signals.

* * * * *